(12) United States Patent
Grodzins et al.

(10) Patent No.: US 7,634,052 B2
(45) Date of Patent: Dec. 15, 2009

(54) TWO-STAGE X-RAY CONCENTRATOR

(75) Inventors: Lee Grodzins, Lexington, MA (US); Hal Grodzins, Cambridge, MA (US)

(73) Assignee: Thermo Niton Analyzers LLC, Billerica, MA (US)

( * ) Notice: Subject to any disclaimer, the term of this patent is extended or adjusted under 35 U.S.C. 154(b) by 16 days.

(21) Appl. No.: 11/681,828

(22) Filed: Mar. 5, 2007

(65) Prior Publication Data
US 2008/0095319 A1    Apr. 24, 2008

Related U.S. Application Data

(60) Provisional application No. 60/853,875, filed on Oct. 24, 2006.

(51) Int. Cl.
*G01N 23/223* (2006.01)
*G21K 1/06* (2006.01)
*H01J 35/02* (2006.01)

(52) U.S. Cl. .............................. 378/44; 378/84; 378/90; 378/140

(58) Field of Classification Search .................... None
See application file for complete search history.

(56) References Cited

U.S. PATENT DOCUMENTS

| | | | | |
|---|---|---|---|---|
| 3,515,874 A * | 6/1970 | Raymond et. al. | ............. | 378/37 |
| 4,048,496 A | 9/1977 | Albert | ......................... | 250/272 |
| 4,260,885 A * | 4/1981 | Albert | ......................... | 378/45 |
| 4,553,253 A * | 11/1985 | Petersen | ...................... | 378/84 |
| 4,599,741 A * | 7/1986 | Wittry | ......................... | 378/85 |
| 4,726,047 A * | 2/1988 | Brouwer et al. | ................ | 378/73 |
| 5,042,059 A * | 8/1991 | Watanabe et al. | ............ | 378/145 |
| 5,497,008 A * | 3/1996 | Kumakhov | ............... | 250/505.1 |
| 5,982,847 A * | 11/1999 | Nelson | ......................... | 378/47 |
| 6,389,100 B1 * | 5/2002 | Verman et al. | ................. | 378/84 |
| 6,389,101 B1 * | 5/2002 | Levine et al. | .................. | 378/85 |

(Continued)

FOREIGN PATENT DOCUMENTS

WO    WO 2007/088938    9/2007

OTHER PUBLICATIONS

Gao et al., "Monolithic polycapillary focusing optics and their applications in microbeam x-ray fluorescence", Appl. Phys. Lett. 69 (11), pp. 1529-1531, Sep. 9, 1996.

Uschmann et al., "*High efficiency high quality X-ray optic based on ellipsoidally bent highly oriented pyrolytic graphite crystal for ultrafast X-ray diffraction experiments*", Applied Optics, OSA, Optucal Society of America, Washington,DC, vol. 44, No. 24, Aug. 20, 2005, pp. 5069-5075, XP009099741 ISSNL 0003-6935 the whole document.

(Continued)

*Primary Examiner*—Edward J Glick
*Assistant Examiner*—Thomas R Artman
(74) *Attorney, Agent, or Firm*—Sunstein, Kann, Murphy & Timbers LLP

(57) ABSTRACT

A method for obtaining a concentrated, monochromatic x-ray beam from a standard x-ray tube or other source of polychromatic emission. X-rays from the anode of the x-ray tube fluoresce an adjoining, independent target that produces a monochromatic spectrum, a portion of which is focused by the x-ray optical system. This two-stage method gives the system considerably versatility without undue loss in signal. The two-stage concentrator makes practical the use of focusing optics in hand-held and portable instruments.

13 Claims, 9 Drawing Sheets

U.S. PATENT DOCUMENTS

| | | | |
|---|---|---|---|
| 7,076,026 B2 * | 7/2006 | Verman et al. | 378/85 |
| 7,180,981 B2 * | 2/2007 | Wang | 378/124 |
| 2003/0142781 A1 * | 7/2003 | Kawahara et al. | 378/44 |
| 2008/0084966 A1 | 4/2008 | Aoki et al. | 378/140 |

OTHER PUBLICATIONS

International Searching Authority, International Search Report & Written Opinion of the International Searching Authority; PCT/US2007/08221, dated May 23, 2008, 17 pages.

* cited by examiner

US 7,634,052 B2

TWO-STAGE X-RAY CONCENTRATOR

The present application claims priority from U.S. Provisional Patent Application Ser. No. 60/853,875, filed Oct. 24, 2006, which is incorporated herein by reference.

TECHNICAL FIELD

The present invention relates to methods and devices for concentrating, and concurrently spectrally filtering, x-rays from a broadband source.

BACKGROUND ART

Simple collimation of x-rays in conjunction with tight geometries allow hand-held analyzers based on x-ray fluorescence (XRF) to achieve high-level performance on centimeter-scale targets. FIG. 1 shows a schematic of the arrangement of components of an XRF analyzer, typified by Niton XRF analyzers manufactured by Thermo Electron Corporation, and designated, generally, by numeral 10. An x-ray tube x-ray tube 100 emits a broad spectrum of x-ray emission 112 due to the acceleration of electrons (or other charged particles) 114 toward a target, referred to herein, without limitation, as anode 116. The energy spectrum of x-ray beam 112 is tailored by one or more x-ray filters 118, collimated by collimator 126 to form collimated beam 128, and directed (by pointing the instrument 10) toward a sample 120 (otherwise referred to, herein, as a "target"). Fluorescent x-rays 122 emitted by the sample are detected by detector 124.

Typical target areas interrogated by x-ray beam 112 are greater than 5 mm$^2$, while typical target-to-anode and target-to-detector distances are less than 15 mm. In the Niton XL model XRF analyzer, the length of the x-ray tube is less than 5 cm.

The upper curve 200 of FIG. 2 shows the output intensity versus energy spectrum from a prior art gold-anode x-ray tube source operating at 50 keV. The bremsstrahlung continuum spectrum 200 is not optimum for measuring low concentration levels. The signal to noise for a given atomic element can be increased substantially by shaping the beam with filters. The lower curve 202 of FIG. 2 is an example of a filtered spectrum that is especially useful for measuring the 23.2 keV characteristic x-rays of the toxic element cadmium whose K electrons are bound with an energy of 26.7 keV. The gain in signal to noise over that obtained with an unfiltered spectrum more than a factor of 10.

X-ray focusing optics can increase the useful flux from an x-ray tube onto a target by orders of magnitude. As used herein and in any appended claims, the term "focusing optics" refers to any member of the class of devices that increase the intensity of the x-rays on a target over that which would be obtained if the optics were not used. The terms "x-ray lens" and "x-ray concentrators" are used herein as equivalent to "focusing optics," without limitation, unless the context dictates otherwise.

Basic elements of an exemplary prior art method for focusing x-rays are described with reference to FIG. 3. The x-ray production region 301 on the anode 116 of x-ray tube 100 is the "object" (in an optical sense) of the focusing element 303 that concentrates a portion of the x-ray spectrum onto the target 120, with an illuminated area typically less than 0.1 mm$^2$. X-ray production region 301 may sometimes be referred to as an x-ray production "point." To achieve this concentration, the size of the electron beam spot 305 on the anode 116 is typically commensurate with the resolution on the target. It is to be understood that other polychromatic sources of x-ray radiation, such as linacs, etc., may serve as x-ray sources within the scope of the present invention. Absorber 309 absorbs x-rays that do not impinge on focusing element 303 but may otherwise impinge on the target 120.

Practical optical concentrators are generally categorized on the basis of whether they make use of total reflection or Bragg scattering. The total reflection method makes use of the fact that the index of refraction of materials is less than unity for electromagnetic waves in the x-ray energy region. The condition for total reflection from a smooth glass surface is, to good approximation, $E\theta \leq 30$, where E is the x-ray energy in keV and $\theta$ is the incident angle, in milliradians, with respect to the medium surface. For example, 30 keV x-rays are totally reflected for all incident angles less than about 1 mradian, or, at a fixed incident angle of 1 mradian, all x-rays less than about 30 keV will be totally reflected.

Bragg scattering, sometimes referred to as crystalline scattering, makes use of the fact that x-rays can be coherently scattered from an oriented crystal. The condition for Bragg scattering is that $2 d \sin \theta = 12.4 \, n/E$, where $\theta$ and E are, as above, the angle of incidence with respect to the planes of the crystal and the x-ray energy in keV, d is the distance between planes of the crystal (the lattice spacing) in Angstroms, and n, the order number, is an integer that is typically either 1 or 2. Example: Using a crystal with a d spacing of 2 Å, the first order Bragg scattering for 30 keV occurs at an angle $\theta = 5.9°$.

Both the total reflection and Bragg scattering techniques are used in energy-dispersive and angular-dispersive, laboratory x-ray spectrometers. The size, weight and power requirements of these spectrometers have hitherto been incompatible with hand held or portable XRF spectrometers that must not weigh more than a few pounds and must have a battery life of many hours. The method described here makes the x-ray optical systems useful as a concentrator for hand-held XRF systems.

SUMMARY OF THE INVENTION

In accordance with preferred embodiments of the present invention, a two-stage concentrator is provided for illuminating a target with highly concentrated x-ray radiation. The concentrator has a polychromatic source of x-ray radiation, the x-ray radiation emanating from an x-ray production region, a converter disposed in substantial abutment to the x-ray production region for generating a substantially monochromatic beam of x-rays, and a focusing element for converging the substantially monochromatic beam of x-rays onto the target.

In accordance with other embodiments of the invention, the x-ray production region may be an anode onto which an energetic beam of particles is impelled, and the x-ray production region may be an x-ray tube.

In further embodiments, the converter is one of iron, zinc, molybdenum, silver, tellurium, bismuth, or thorium, and, generally, may be composed of a material and characterized by a thickness greater than one tenth, and less than ten times, a mean free path of the monochromatic beam of x-rays within the material. The focusing element may be a Bragg reflector, and. Moreover, it may be a truncated ellipsoid, and, additionally or alternatively, highly-oriented pyrolitic graphite.

In accordance with another aspect of the invention, an x-ray illuminator is provided that has a plurality of two-stage concentrators, each two-state concentrator in accordance with any of the foregoing summary. Each of the two-stage concentrators may be comprised substantially of a distinct elemental material. The plurality of two-stage concentrators may be disposed within a sequencing mechanism that may be a rotating cylinder or a translating shuttle, or another configuration allowing the two-stage concentrators to be inserted sequentially.

In accordance with yet another aspect of the invention, a method for illuminating a target with highly concentrated x-ray radiation. The method has steps of:
a. creating first-stage beam of polychromatic x-ray radiation;
b. converting the polychromatic x-ray radiation to a substantially monochromatic beam of x-ray radiation; and
c. focusing the substantially monochromatic beam of x-ray radiation onto the target.

In particular embodiments of the invention, the step of converting the polychromatic x-ray radiation to a substantially monochromatic beam of x-ray radiation may include passing the polychromatic x-ray radiation through a material characterized by Kα radiation between 6 keV and 28 keV.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS OF THE INVENTION

Figure 1:
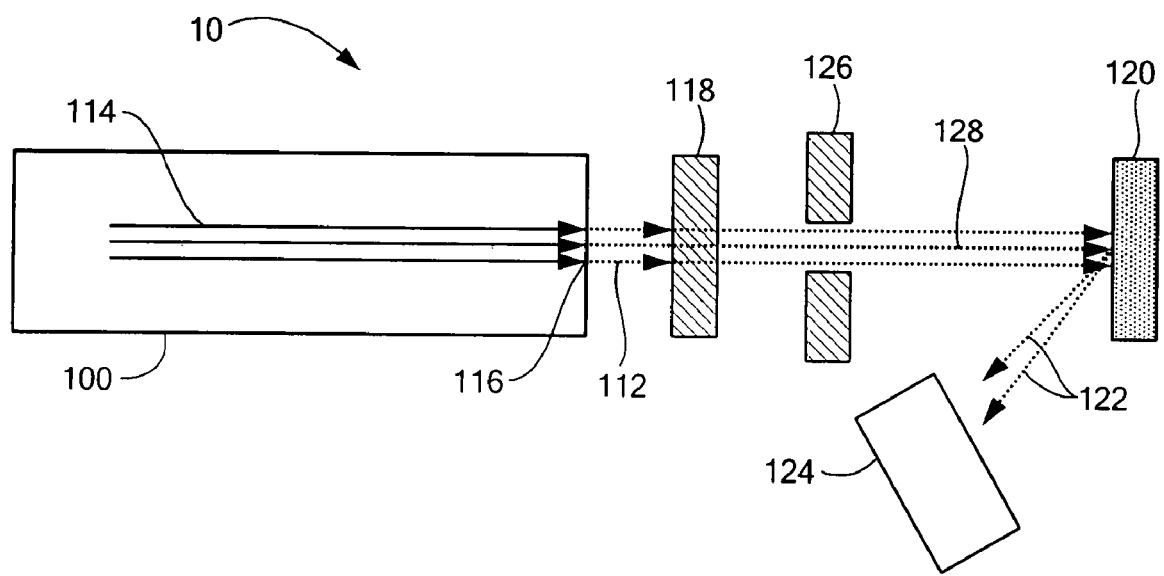
FIG. 1 is schematic depiction of salient components of a prior art x-ray fluorescence instrument.
Figure 2:
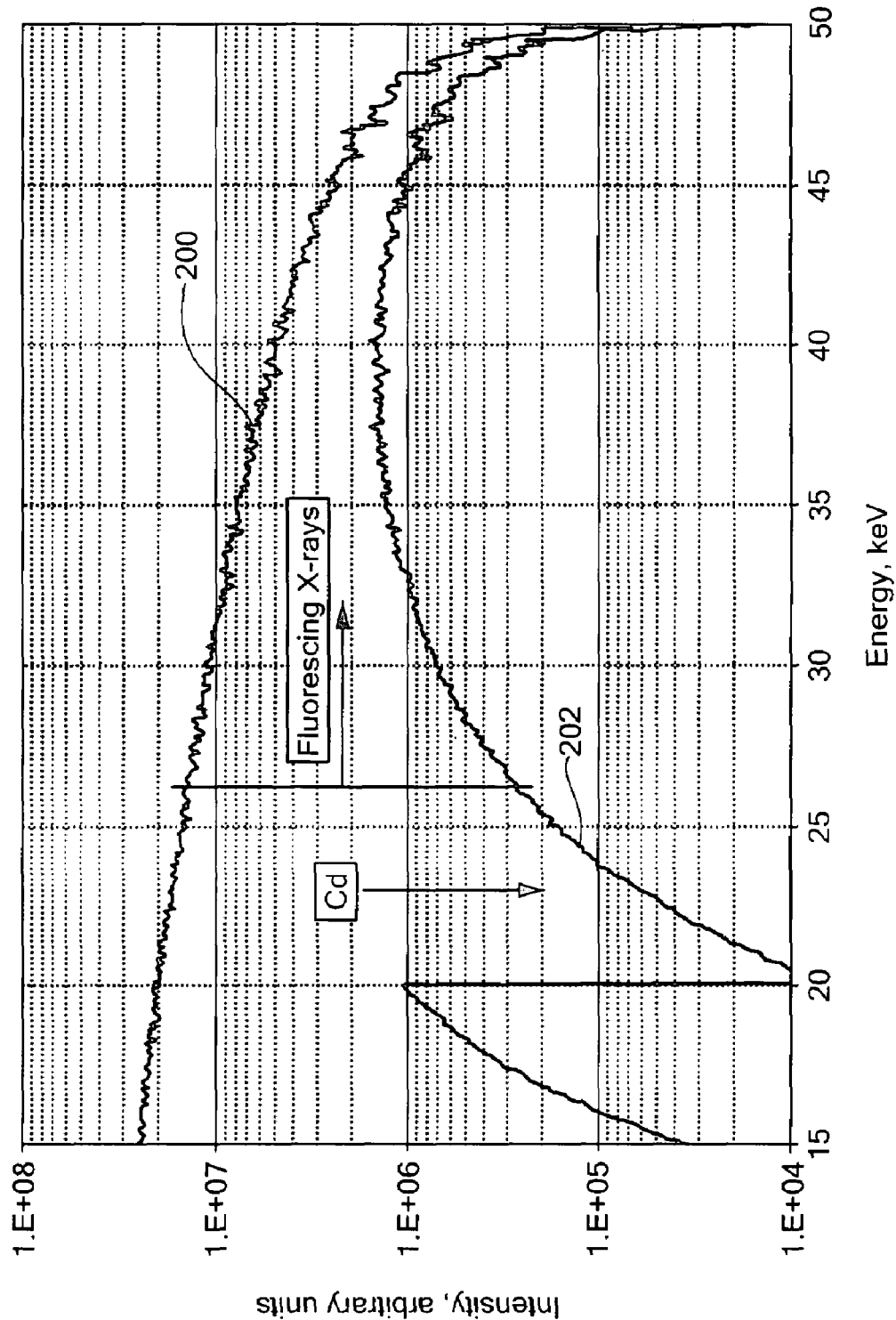
FIG. 2 shows the output intensity versus energy spectrum of a prior art x-ray source, before and after filtering.
Figure 3:
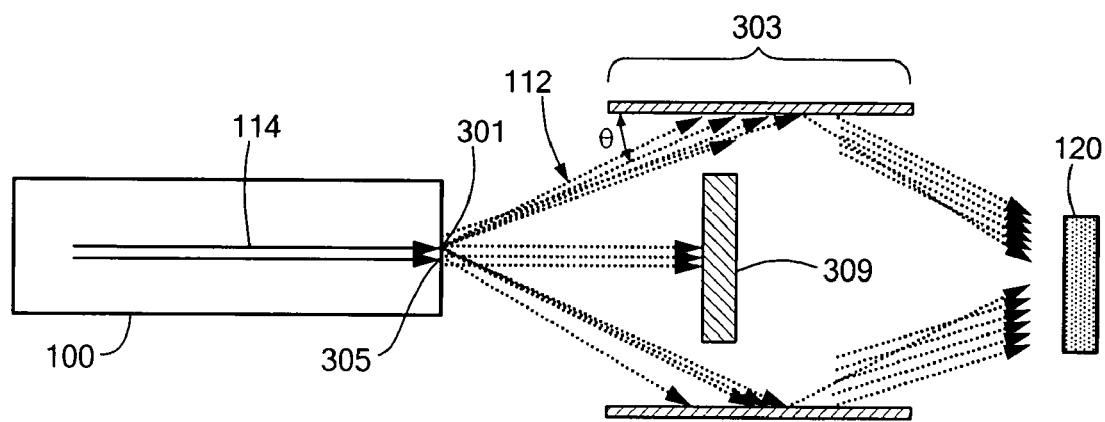
FIG. 3 depicts basic elements of a prior art optical system used to concentrate x-rays.

In prior art x-ray focusing systems such as that depicted in FIG. 3 and described in the foregoing Background Section, which may be referred to herein as based on single-stage concentrators, the anode 305 of x-ray tube 100 is the object of the x-ray optical lens formed by focusing element 303.

In accordance with preferred embodiments of the present invention, now described with reference to FIG. 4, a converter 400 is interposed, directly adjacent to anode 305 of x-ray tube 100 so as to convert the emitted x-rays 402, referred to herein as "first-stage" x-rays, into x-rays 404 characterized by a nearly monochromatic x-ray spectrum, referred to herein as the "second stage x-ray spectrum." Converter 400 is now the new object of the x-ray optical lens. The method depicted may be referred to herein as a "Two-Stage Concentrator" (TSC). The optimal composition, size and thickness of the converter are selected, based upon principles to be described, in accordance with parameters of particular applications.

The method described is particularly suited to the Bragg concentrators but may also have advantages for concentrators based on total reflection.

Figure 4:
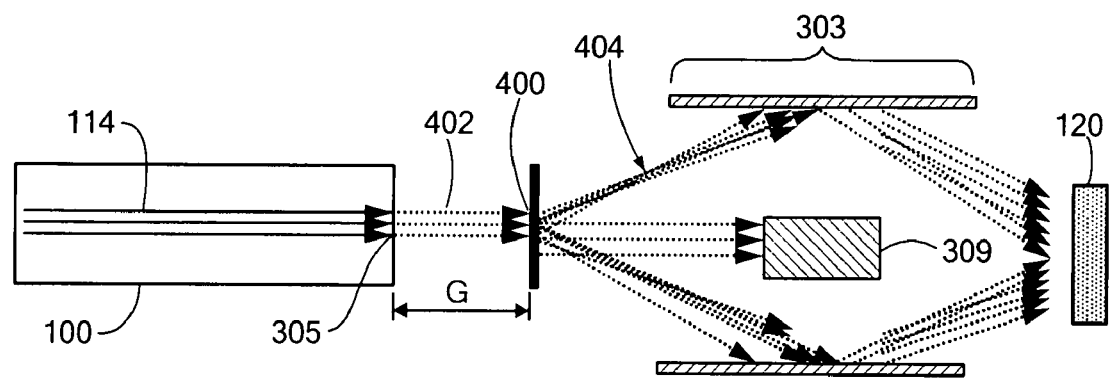
FIG. 4 depicts a two-step process of spectral and spatial concentration of x-rays, in accordance with embodiments of the present invention.

The space denoted G, between anode 305 and the new object of the focusing optics at converter 400, is greatly exaggerated in FIG. 4 to show the two-stage process clearly. In practice, in preferred embodiments of the invention, converter 400 advantageously adjoins anode 305 in order to maximize the efficiency of conversion. The abutment of the converter to the anode is a key feature of the two-stage concentrator in preferred embodiments of the invention.

The geometrical efficiency depends on the gap G and the diameter of the converter. If the electron spot size is negligible (i.e., effectively a point source) then the relation is just the solid angle equation: $\Omega=0.5(1-\cos\theta)$. In this idealized case, if the gap is twice the converter radius then the geometrical efficiency of conversion has dropped by a factor of 10. The calculation reflected in the plots of FIGS. 5 and 6, takes into account the finite size of the electron beam spot and reflects a further reduction in geometrical efficiency. For a concentrator of 1:1 magnification and a target spot size of 200 microns, the converter radius is 100 microns and the gap G should not be more than 200 μm.

Figure 5:
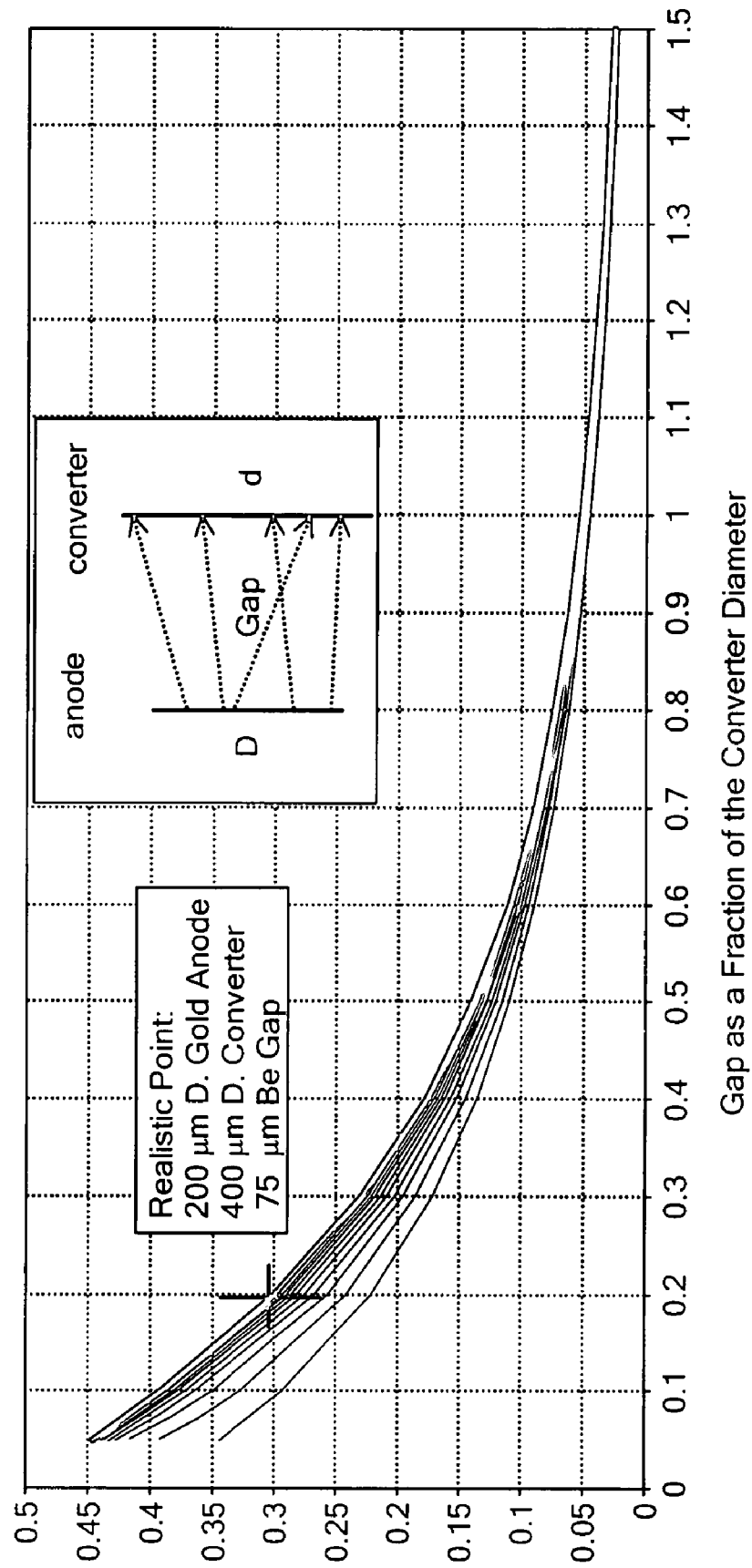
FIG. 5 shows a plot of the calculated fraction of the primary x-rays intercepted by the converter, in accordance with embodiments of the present invention, as a function of the gap length G, for various ratios of converter to anode diameters.
Figure 6:
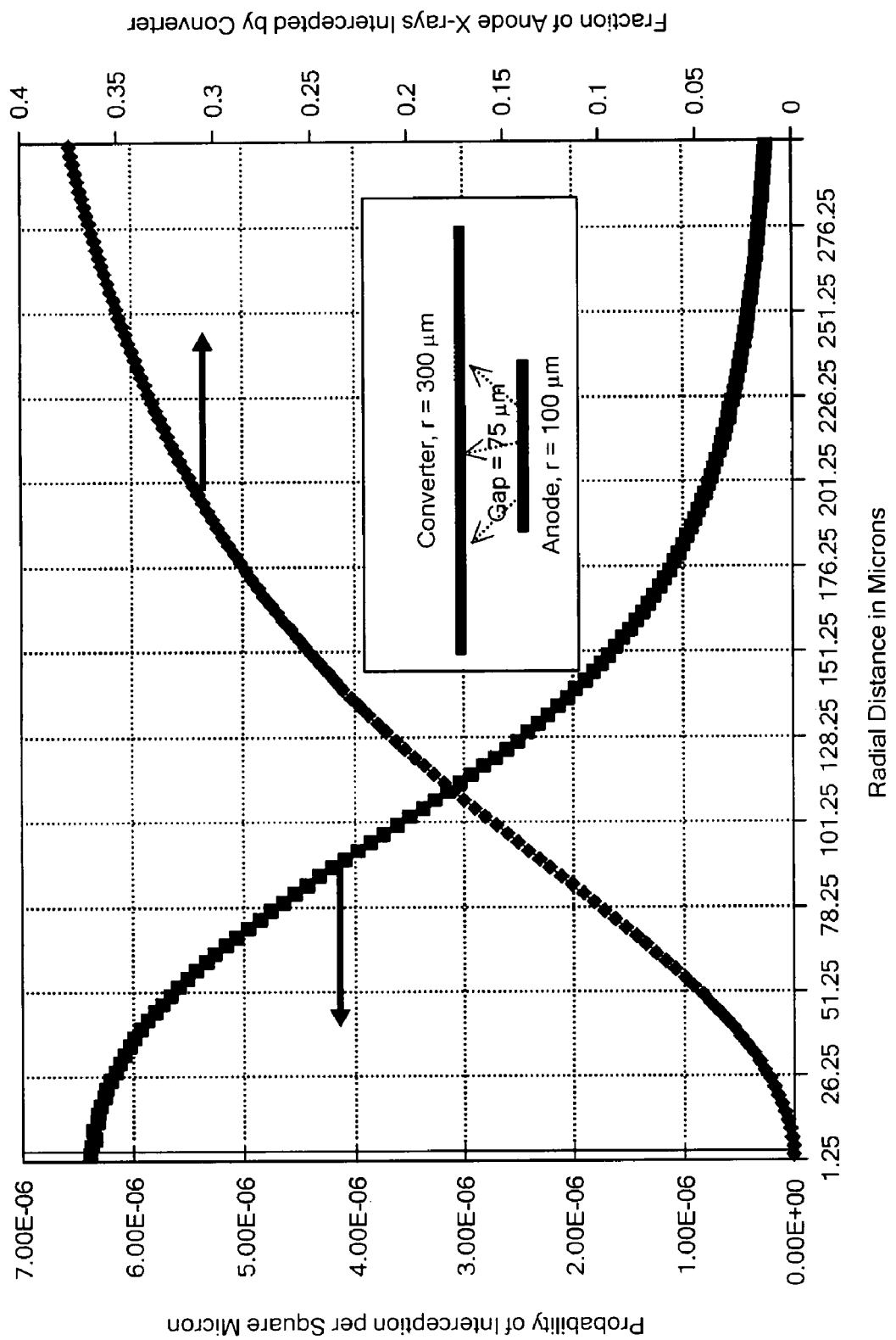
FIG. 6 shows the interception probability of FIG. 5 in greater detail, using the specific example of the cross-point specifications of FIG. 5.

FIGS. 5 and 6 demonstrate the critical nature of the gap G in a quantitative way. FIG. 5 shows the fraction of the primary x-rays intercepted by the converter, as functions of the gap length and for various ratios of converter to anode diameters. The x-axis is the gap width G in units of the converter diameter. The converter diameter, d, is in units of the beam diameter at the anode.

The maximum fraction that can be intercepted is 0.5 since half of the first stage x-ray spectrum from anode 305 is emitted in the back hemisphere. The cross point indicated in FIG. 5 represents one practical set of parameters: a 200 μm diameter electron beam strikes an anode constituted by 2 μm of gold on a 75 μm thick beryllium window; with a 400 μm diameter converter abutting the beryllium. These parameters result in 30% of the bremsstrahlung being intercepted by the converter.

FIG. 6 shows the interception probability in greater detail, using the specific example of the cross-point specifications of FIG. 5. The probability of interception, per unit area, has a Gaussian-like form with the maximum at the center of the converter. The cumulative fraction of all the x-rays emitted by the anode reaches 30% at a converter radius of 200 μm.

Thickness of the Converter

The converter material is chosen to create the desired monochromatic characteristic x-ray for the specific application; e.g. iron, molybdenum and tellurium produce 6.4 keV, 17.5 keV and 27.5 keV monochromatic radiation, respectively. It should be noted that there is generally more than one converter element that will yield nearly the same monochromatic x-ray energy. For example, the $K_\beta$ line of In is 23.3 keV, within 1% of the $K_{\alpha 1}$ line of Te. There may be applications where the In converter is a more appropriate converter.

Figure 7:
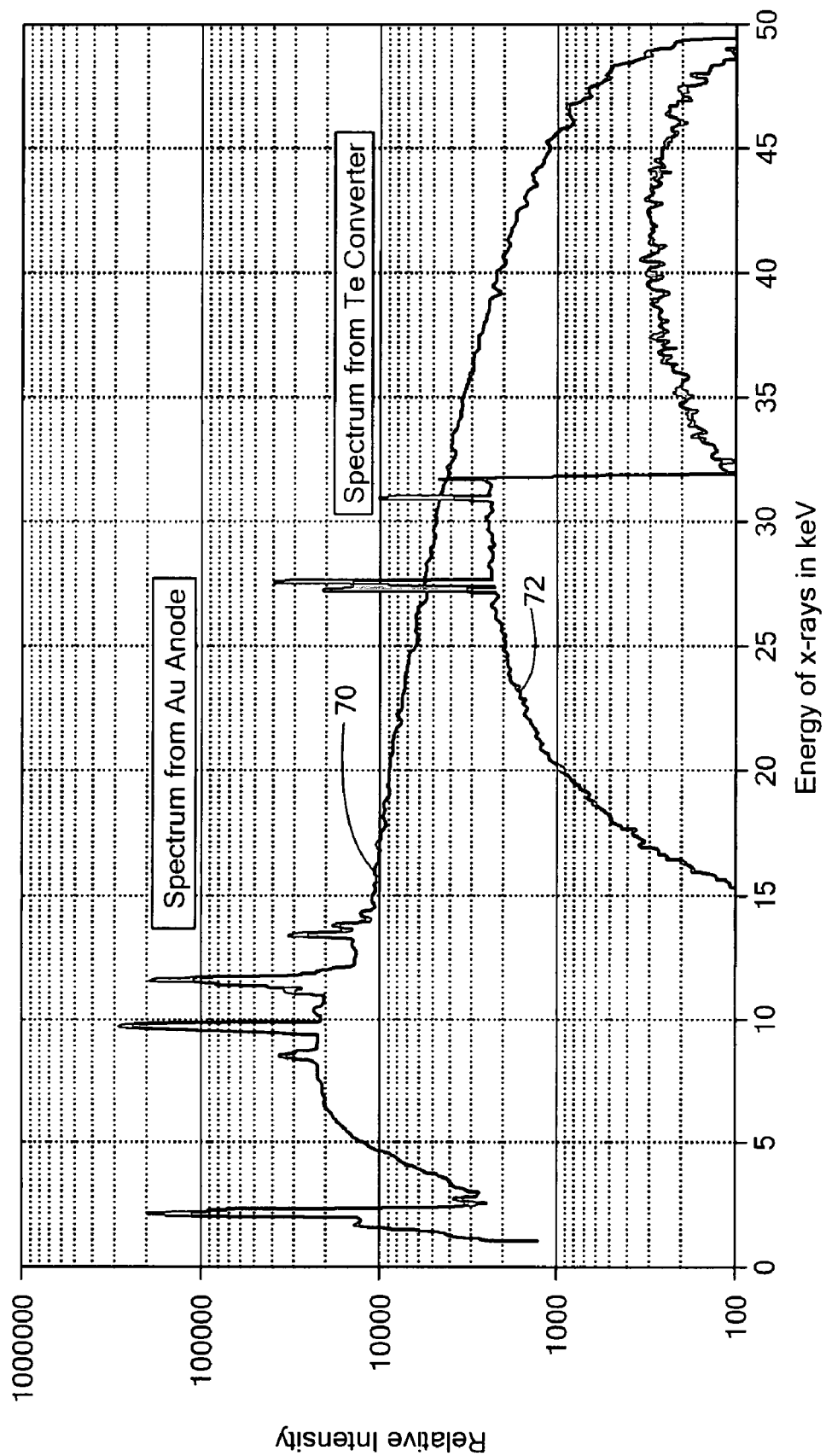
FIG. 7 is a log plot of the Monte Carlo spectra calculated for a 50 keV electron beam incident on a 2 μm gold anode, and of the spectrum following a 150 μm tellurium converter disposed 75 μm from the gold anode.
Figure 8:
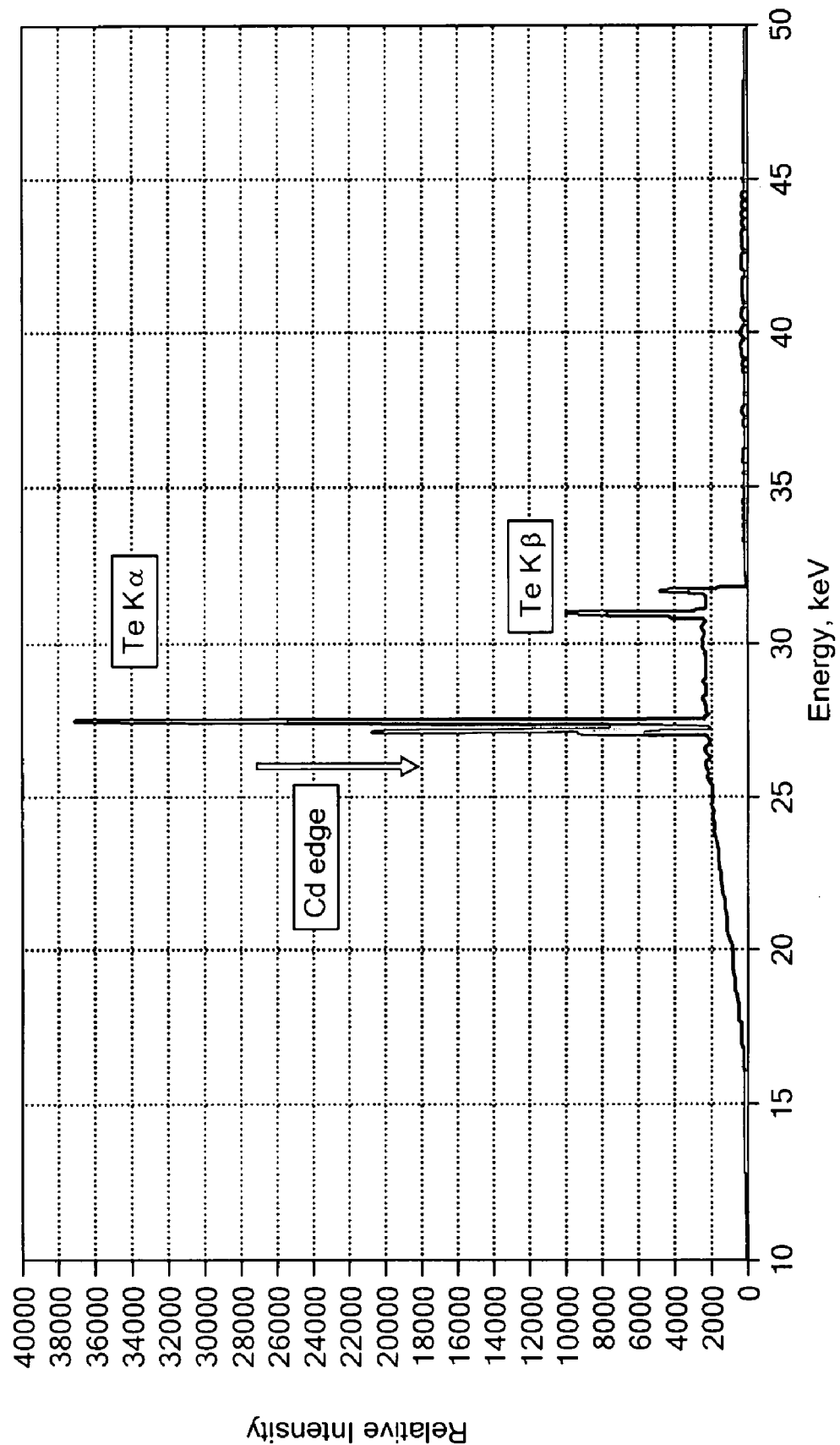
FIG. 8 is a linear plot of the lower curve of FIG. 7 to show clearly the strength of the monochromatic characteristic x-rays of tellurium compared to the continuum.

The thickness of the converter material is chosen to maximize the signal to noise of the sought-for signals. In general, the thickness of the converter will be within an order of magnitude of the mean free path of converter x-rays in the converter material, i.e., between one-tenth and ten times the mean free path of converter x-rays in the converter material. For example: The mean free path in tellurium, of the 27.5 keV $K_\alpha$ x-rays of tellurium, is 175 µm. Converter thickness ranging from 100 µm to 175 µm have high conversion efficiencies. FIG. 7 shows an example: FIG. 7 is a log plot of the Monte Carlo spectra calculated for the preferred embodiment example below. The upper curve 70 is the spectrum of characteristic lines and continuous bremsstrahlung from a 50 keV beam of electrons on a 2 µm Au anode. The lower curve 72 shows the spectrum that emerges in the forward direction from a 150 µm thick tellurium converter that is 75 µm from the Au anode. FIG. 8 is a linear plot of the spectrum from the converter showing the high degree of monochromaticity of the forward-directed beam.

The two-stage converter described herein, in accordance with embodiments of the present invention, advantageously obviates the need for either a special x-ray tube or a special alignment of the x-ray tube and the concentrator. The result is a lightweight, small XRF system that uses no greater power than traditional hand-held instruments. Similarly, a two-stage concentrator may be applied advantageously in other x-ray systems such as transportable systems, bench-top and laboratory systems, as well as wave-length dispersive spectrometers.

In order to appreciate the advantages and disadvantages of the two-stage focused beam method, it is usefully compared to the collimated beam method and to the traditional single-stage focused beam method. The two-stage method, while not providing as much total power onto the target as the single-stage method, is more than an order of magnitude more effective than the collimated beam method. The comparison is made for the preferred application of measuring the toxic element cadmium in plastics, soils and other matrices.

An Exemplary Embodiment

Figure 9:
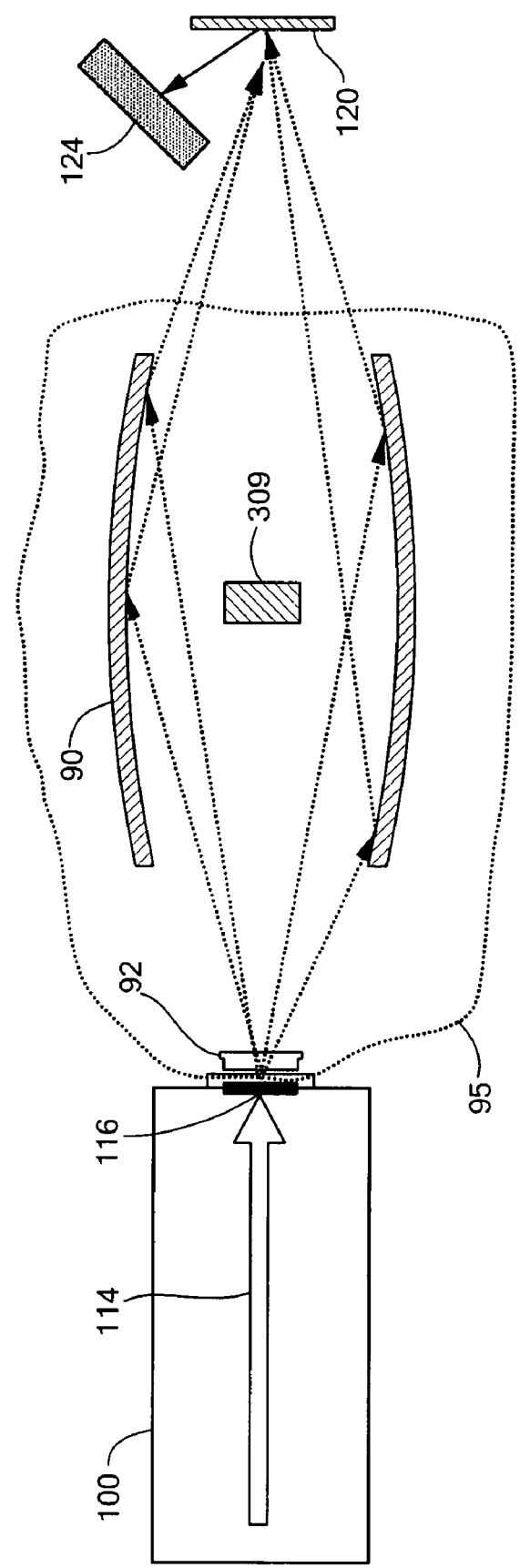
FIG. 9 is a schematic depiction of elements of an XRF system using a two-step concentrator of a tellurium converter at the focal point of a HOPG ellipsoid lens, in accordance with embodiments of the present invention.

In accordance with an exemplary embodiment, described with reference to FIG. 9, a concentrated beam of 27.5 keV monochromatic x-rays is provided for the XRF measurement of low levels of cadmium, a toxic element whose concentration in materials is regulated. While specific values chosen for this application are recited, it is to be understood that, within the scope of the invention, the values of all of the parameters can vary over wide ranges to suit different applications.

The Bragg condition for coherent reflection can be satisfied by a broad range of geometries. One geometric arrangement of components, shown in FIG. 9, uses a truncated ellipsoid 90 of highly-oriented pyrolytic graphite (HOPG) for first-order scattering of 27.5 keV x-rays. The truncated ellipsoid 90 is 3 cm long; the internal diameter at the center is 4.2 mm. The tellurium converter 92 is at the left focal point, 4.5 cm from the ellipsoid center; the target 120 is 4.5 cm to the right.

The Te converter 92 plus ellipsoidal focusing optics 90 comprise a single, rigid, independent unit that we will call for convenience the Concentrator 95. The transmission x-ray tube has a gold anode on its 75 µm thick Be end window. The tellurium converter abuts the Be so the gap G, shown schematically in FIGS. 4-6, is 75 µm. The alignment of concentrator 95 with respect to the x-ray tube is not critical, as is the case for the single-stage method.

The 0.4 mm diameter tellurium converter 92 intercepts 30% of the x-rays generated in the Au anode 305 and converts approximately 35% of the intercepted x-rays above 31.7 keV into Te Kα x-rays of 27.5 keV. The geometrical efficiency of the ellipsoid 90 is about $10^{-3}$. The reflective efficiency of the HOPG coated ellipsoid 90 is ~35%. These values allow a first order comparison among the three methods described above.

Table 1 shows the results of model calculations for a 0.4 mm target, which is the same diameter as the converter: the ellipsoid has a 1:1 magnification We have assumed a 20 µA beam of 50 keV electrons (1 Watt) on a 75 µm thick Be anode coated with 2 µm thick layer of Au.

TABLE 1

Relative Effectiveness of Two-Step Optics, One-Step Optics and Collimation

|  | Two Stage HOPG Au Anode + Te Converter | Single Stage HOPG Te Anode | Collimation Only Au anode |
|---|---|---|---|
| Electron Flux: 20 µA | $1.2 \times 10^{14}$ | $1.2 \times 10^{14}$ | $1.2 \times 10^{14}$ |
| e to x-ray: 2 µm Au, 50 keV (p/e/sr) | $7 \times 10^{-4}$ | $4 \times 10^{-4}$ | $7 \times 10^{-4}$ |
| Fraction of x-rays > E(Te/Cd edge) | 0.07 | 0.12 | 0.12 |
| Au Spectrum to Te K x-ray conversion | 0.35 | — | — |
| Geometric loss due to gap between anode material (Au) and converter | 0.3 | — | — |
| Absorption by filters | — | — | 0.3 |
| PE Efficiency gain for exciting Cd* | 10 | 5 | |
| Geometric efficiency, sr** | $10^{-3}$ | $10^{-3}$ | $2 \times 10^{-5}$*** |
| Fraction reflected | 0.35 | 0.35 | — |
| 27-28 keV flux on 0.3 mm D target | $2 \times 10^{6}$ | $10^{7}$ | $6 \times 10^{4}$ |

*The Te converter converts a significant portion of the x-rays above 31.8 keV into 27 keV x-rays. The lower excitation energy has a significantly larger probability of fluorescing cadmium than the x-rays from 31.8 keV to 50 keV.
**The geometrical solid angle is from the tellurium focal point to the lens in the HOPG methods and to the target in the collimation method, which is assumed to be 20 mm from the tube anode.
***Assumes a 0.3 mm collimation at 15 mm.

The comparative results for the specific example of Table 1 illustrate the general conclusion that to obtain the highest intensity in a small target spot, the two-stage converter with focusing optics is significantly less effective than is focusing optics without the conversion, but is significantly more effective than simple collimation without the use of focusing optics.

The two-step method has secondary advantages that make it attractive for situations where low weight and power are important.

The Concentrator, being independent of the x-ray tube, can be used with the same x-ray tube to produce a concentrated beam of energies ranging from a few keV to 100 keV by the proper choice of the high voltage of the x-ray tube and the converter element. A rough rule of thumb is that the high voltage should be between 1.5 and 2 times the K binding energy of the converter element. The choice of converter element requires consideration of its fluorescent yield, which is the ratio of the number of x-rays emitted to the number of excitations, a quantity that drops rapidly as the atomic number drops below 30. Tellurium (Z=52), zinc (Z=30), iron (Z=26), Ca (Z=20) and Al (Z=13) have fluorescent yields of 87%, 50%, 33%, 17% and 4% respectively.

The choice of converter suited for a specified application may be informed by the following non-exhaustive list of considerations:

The element or elements that are intended to fluoresce in the sample: Te $K_\alpha$, (or In $K_\beta$) are excellent choices for detecting Cd, and may also be used for detecting Pb, with its L electron edge around 15 keV.

Elements whose fluorescence is to be avoided. When Cd (Z=48) is to be fluoresced, it is often desirable to avoid the fluorescence of Sb (51) or Sn (50), which give unwanted backgrounds in the Cd region. The $K_\beta$ of Te at 31 keV excites both. Indium's $K_\beta$ line at 27.3 keV excites the Cd, with only 20% the effectiveness of the Te Ka, but it cannot excite either Sn or Sb. In view of the finite, and sometimes substantial, acceptance bandwidth of the HOPG, the In may be preferable.

The energy of the electrons that generate the primary bremsstrahlung.

The availability of the converter material in a stable form. It is worth noting that the two-stage concentrator, with the converter element in air, allows the use of a far wider range of elements than is generally permissible in the single stage version of FIG. 3. In that version, the anode element on a beryllium substrate is in a vacuum and must dissipate the power deposited by the electrons.

Figure 10:
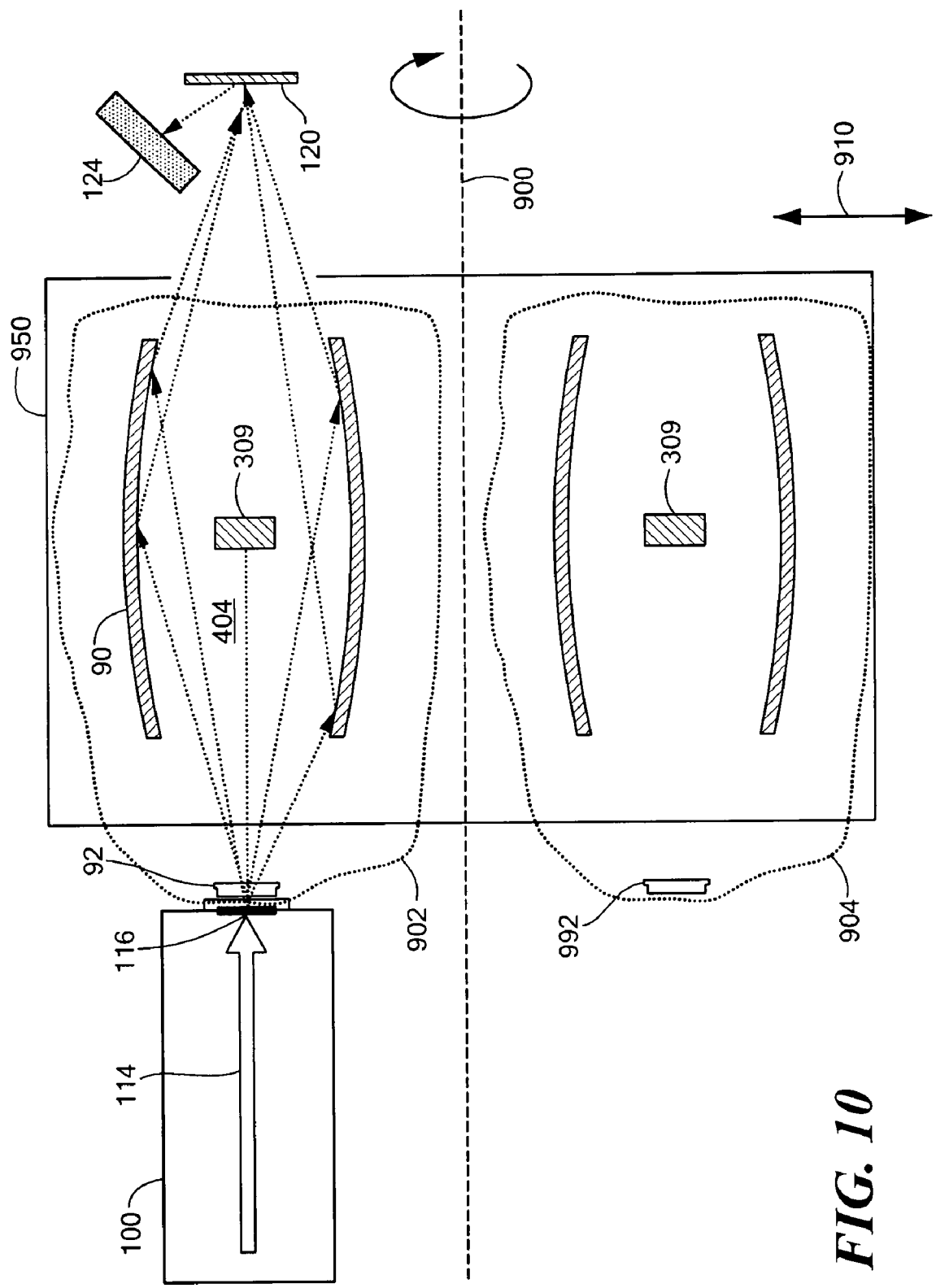
FIG. 10 is a schematic depiction of an XRF system using a plurality of two-step concentrators, each having a converter at the focal point of a HOPG ellipsoid lens, such that the concentrators may be inserted sequentially between a source and a sample in accordance with embodiments of the present invention.

In accordance with various alternate embodiments of the invention, concentrators, insofar as they may be independent of the x-ray tube, can be multiplexed in a gun-barrel arrangement, for example, so that different monoenergetic energies can be sequentially selected for fluorescing the target. An exemplary embodiment is now described with reference to FIG. 10. Multiple Concentrators 902, 992 are coupled to a sequencing mechanism 950 which allows for their sequential insertion between source 100 and sample 120. Sequencing mechanism 950 may be a shuttle or carriage that allows for translation in a direction 910 substantially perpendicular to x-ray beam 404 such that Concentrator 992 can be positioned to replace Concentrator 902 in the path between source and sample. Alternatively, mechanical structure 950 may be a cylinder configured to rotate about axis 900, again positioning multiple Concentrators seriatim. Each Concentrator may have a converter 92, 992 of a distinct elemental composition, such that monochromatic x-rays of a different energy are provided at each position of the sequencing mechanism 950.

The following two applications are illustrative.

A Concentrator of Te Ka x-rays at 27.2 keV and 27.5 keV, and a Concentrator of Sn Ka x-rays at 25.0 keV and 25.3 keV to isolate, by subtraction, the intensity of the Cd x-rays; the high voltage of the x-ray tube is unchanged.

A Concentrator of Te Ka x-rays at 27.2 keV and 27.5 keV, using a high voltage of 50 keV, to measure the toxic elements Cd and Pb, and a Concentrator of Fe x-rays at 6.4 keV, using a high voltage of 15 keV to measure the toxic element Cr.

It should be noted that alignment, in accordance with the two-step method is far less critical than is the alignment problem in the one-step focusing method. In the latter, the alignment of the focusing element with the electron spot on the anode is often the most difficult challenge to successful application. In the two-step method, the alignment of the lens object, i.e. the Te in the preferred embodiment, is fixed by the mechanical construction. The alignment of the lens object with the electron beam on the anode is not particularly critical.

Monocapillary and polycapillary optics concentrate x-ray rays up to a maximum energy determined by the critical angle for total reflection. For many applications, the continuous spectrum that impinges on the target is not as effective as a monochromatic beam. At least one commercial polycapillary focusing system is available that produces a monochromatic beam by combining two polycapillary concentrators and one Bragg monochromator. The two-stage Concentrator described herein is a far less expensive, far simpler, and more effective method for producing a nearly monochromatic source for the monocapillary or polycapillary optics.

While the two-stage method has been illustrated in the context of its use for x-ray fluorescence applications, the method is also advantageously applicable to angular-dispersive and energy-dispersive spectroscopy where a small diameter, monochromatic beam of x-rays is needed.

The embodiments of the invention that are described herein are intended to be merely exemplary and numerous variations and modifications will be apparent to those skilled in the art. All such variations and modifications are intended to be within the scope of the present invention as defined in the appended claims.

We claim:

1. A two-stage concentrator for illuminating a target with highly concentrated x-ray radiation of a specified energy, the two-stage concentrator comprising:
    a. a polychromatic source of x-ray radiation, the x-ray radiation emanating from an anode interior to a vacuum enclosure;
    b. a converter disposed exterior to the vacuum enclosure and in substantial abutment to the vacuum enclosure for generating a substantially monochromatic beam of characteristic x-ray line emission of the specified energy; and
    c. a focusing element for re-imaging the substantially monochromatic beam of x-rays onto the target.

2. A two-stage concentrator in accordance with claim 1, wherein the converter is one of iron, zinc, molybdenum, silver, tellurium, bismuth, or thorium.

3. A two-stage concentrator in accordance with claim 1, wherein the converter is composed of a material, and is characterized by a thickness greater than one tenth, and less than ten times, a mean free path of the monochromatic beam of x-rays within the material.

4. A two-stage concentrator in accordance with claim 1, wherein the focusing element is a Bragg reflector.

5. A two-stage concentrator in accordance with claim 1, wherein the focusing element is a truncated ellipsoid.

6. A two-stage concentrator in accordance with claim 1, wherein the focusing element is highly-oriented pyrolitic graphite.

7. An x-ray illuminator, comprising a plurality of two-stage concentrators, each two-stage concentrator in accordance with any one of claims 1 and 2 through 6.

8. An x-ray illuminator in accordance with claim 7, wherein the converter associated with each of the plurality of two-stage concentrators is comprised substantially of a distinct elemental material.

9. An x-ray illuminator in accordance with claim 7, wherein the plurality of two-stage concentrators are disposed within a sequencing mechanism.

10. An x-ray illuminator in accordance with claim 9, wherein the sequencing mechanism is a rotating cylinder.

11. An x-ray illuminator in accordance with claim 10, wherein the sequencing mechanism is a translating shuttle.

12. A method for illuminating a target with highly concentrated x-ray radiation of a specified energy, the method comprising:
    a. creating first-stage beam of polychromatic x-ray radiation within a vacuum enclosure;
    b. converting the polychromatic x-ray radiation to a spot of substantially monochromatic characteristic x-ray line emission of the specified energy by means of a converter disposed externally to the vacuum enclosure; and c. positioning the spot of substantially monochromatic x-ray radiation at an object plane of an x-ray concentrator; and d. re-imaging the substantially monochromatic x-ray radiation onto the target.

13. A method in accordance with claim 12, wherein the step of converting the polychromatic x-ray radiation to a spot of substantially monochromatic x-ray radiation includes passing the polychromatic x-ray radiation through a material characterized by Kα radiation between 6 keV and 28 keV.

* * * * *